United States Patent [19]

Minton et al.

[11] Patent Number: 4,609,991
[45] Date of Patent: Sep. 2, 1986

[54] AUTOMATED SYSTEM FOR DETERMINING THE MOLECULAR WEIGHT AND/OR CONCENTRATION OF MACROMOLECULES VIA SEDIMENTATION EQUILIBRIUM

[75] Inventors: Allen P. Minton, Wheaton; Arun K. Attri, Bethesda; James V. Sullivan, Bowie; Paul Fitze, Mount Airy, all of Md.

[73] Assignee: The United States of America as represented by the Department of Health and Human Services, Washington, D.C.

[21] Appl. No.: 515,169

[22] Filed: Jul. 19, 1983

[51] Int. Cl.[4] .................. G06F 15/46; G01N 1/10
[52] U.S. Cl. .................. 364/499; 73/864.82; 356/246; 356/318; 356/436; 364/497; 364/550
[58] Field of Search ........ 364/167, 415, 416, 497–499, 364/550, 551; 356/246, 319, 331, 436, 307, 318, 320; 250/491.1, 573, 576; 73/864.82; 422/68, 63, 72

[56] References Cited

U.S. PATENT DOCUMENTS

| Re. 31,150 | 2/1983 | Ginsberg et al. | 356/246 X |
|---|---|---|---|
| 3,591,290 | 7/1971 | Baker et al. | 356/436 X |
| 3,918,910 | 11/1975 | Soya et al. | 364/499 X |
| 4,090,789 | 5/1978 | Macemon et al. | 356/246 X |
| 4,178,102 | 12/1979 | Riccardi et al. | 356/307 |
| 4,180,327 | 12/1979 | Maeda et al. | 356/320 |
| 4,255,053 | 3/1981 | Lübbers et al. | 356/318 |
| 4,299,487 | 11/1981 | Sengoku et al. | 356/320 |
| 4,300,833 | 11/1981 | Harnly et al. | 356/307 |
| 4,318,615 | 3/1982 | Sagusa et al. | 356/320 |
| 4,490,040 | 12/1984 | Lucht et al. | 356/318 |

Primary Examiner—Felix D. Gruber
Assistant Examiner—Kevin J. Teskar
Attorney, Agent, or Firm—Browdy & Neimark

[57] ABSTRACT

An automated system for measuring the concentration gradient of centrifuged solute and directly calculating the molecular weight and/or sedimentation coefficient of an optically absorbing solute. Monochromatic light passes through a stationary slit and a previously centrifuged sample in a tube while the tube is moved vertically at a uniform rate by a platform which is driven by a motor and gearing, including a gear nut which drives a vertical screw attached to the platform. The transmitted light impinges on a photodetector which provides absorbance readings. This provides data of absorbance vs. time through the scanning cycle, which is processed digitally. A microcomputer is used to calculate the molecular weight and/or sedimentation coefficient from this data. The centrifuge tube is supported in a transparent cuvette containing a black plastic adaptor block which conformably receives the tube and supports it in upright position, allowing the light beam to pass through opposite vertical slot portions in the block. The cuvette rests on the platform, which is moved vertically relative to the slit defining the fixed beam path. A microswitch is operated at the upper limit of travel to stop the drive motor. The motor is external to the housing in which the optical components and the sample tube are located. The external motor is coupled by a flexible shaft to the drive gearing. Alternatively, a stepping motor may be employed instead of a synchronous motor to move the centrifuge tube in an incremental fashion rather than at uniform velocity.

23 Claims, 7 Drawing Figures

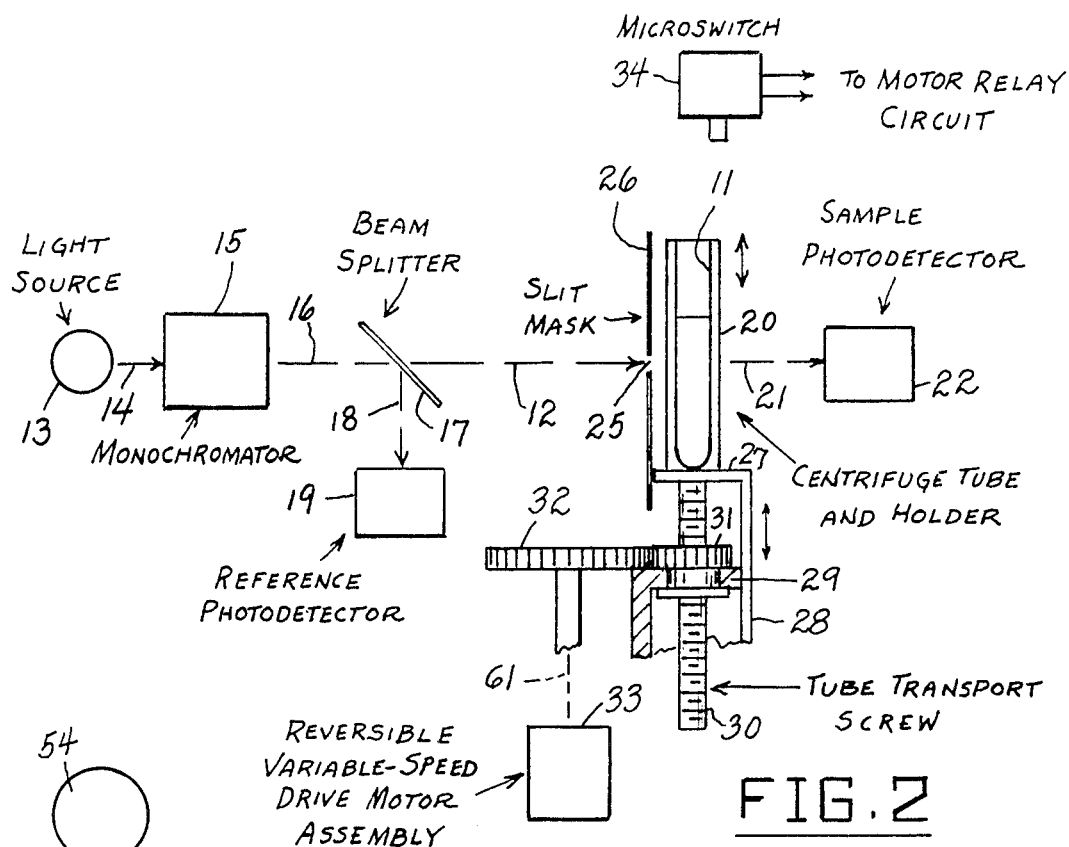
FIG. 2
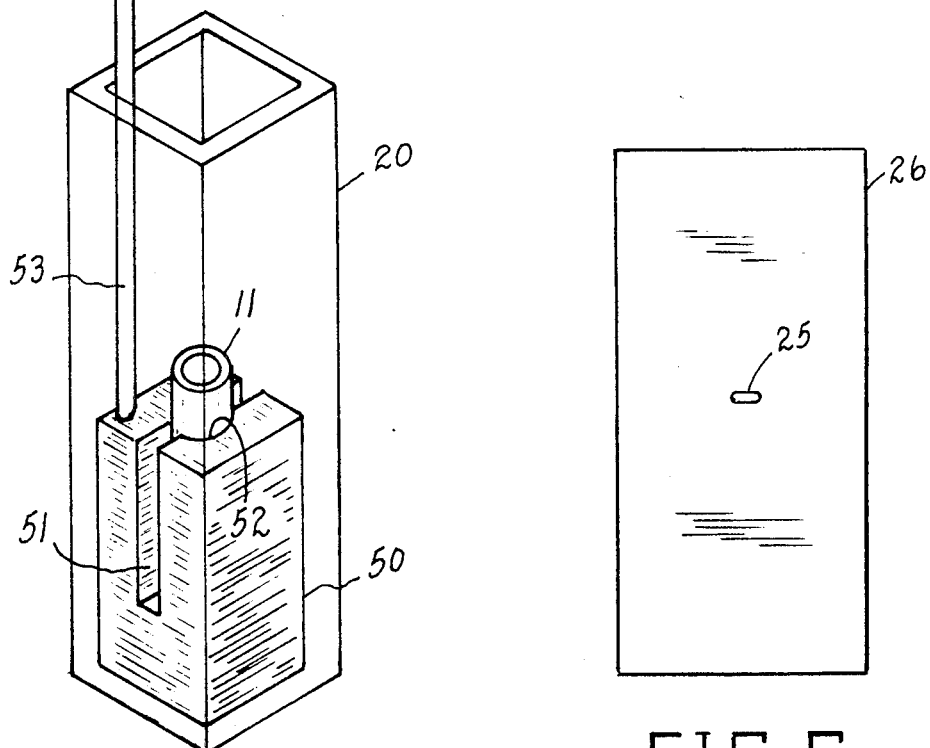
FIG. 5
FIG. 6

AUTOMATED SYSTEM FOR DETERMINING THE MOLECULAR WEIGHT AND/OR CONCENTRATION OF MACROMOLECULES VIA SEDIMENTATION EQUILIBRIUM

FIELD OF THE INVENTION

This invention relates to systems for measuring the molecular weight, sedimentation coefficient and/or the concentration of optically absorbing solute, and more particularly to a method and means for performing such measurements as functions of positions of the optically absorbing solute in a centrifuge tube, and without the need to fractionate the contents of the tube.

BACKGROUND OF THE INVENTION

The determination of molecular weight and sedimentation coefficient via measurement of sedimentation equilibrium is a classical method of macromolecular chemistry and is well described in many textbooks. Until recently the utilization of this method required the use of large and expensive analytical centrifuges which demanded considerable expertise. Recently the molecular weights of proteins via sedimentation equilibrium have been successfully measured using a relatively inexpensive air-driven centrifuge, namely, the Beckman Airfuge. In order to calculate the molecular weight it is necessary to measure the gradient of solute concentration in the centrifuge tube at sedimentation equilibrium. This was accomplished by fractionating the solution in the tube into layers according to vertical position (typically, 10 layers in a 100 microliters sample), and measuring the average concentration of solute in each layer. This operation is tedious and requires manual dexterity, which may explain why the use of the Airfuge for the determination of molecular weights has not become widespread. Moreover, the resolution of the data obtained via manual fractionation is insufficient for precise determination of sedimentation coefficient. There is a definite need for a system to automatically measure the gradient of solute concentration in the centrifuge tube and to interpret the measured gradient with minimal user manipulation or other intervention, with smaller samples than heretofore required, and using generally available preparative ultracentrifuges, as well as the Beckman Airfuge.

There is also a definite need for a system enabling the concentration of solute to be automatically determined as a function of position in the centrifuge tube, without the need to fractionate the contents of the tube, which would also enable completely automatic determination of molecular weight and/or sedimentation coefficient.

A preliminary search of the prior art revealed the following prior U.S. patents of interest in connection with the present invention: Marcovecchio et al, U.S. Pat. No. 3,442,593; Decker, U.S. Pat. No. 3,578,980; Itoi et al, U.S. Pat. No. 4,063,817; Riccardi et al, U.S. Pat. No. 4,178,102; Maeda et al, U.S. Pat. No. 4,180,327; Lubbers et al, U.S. Pat. No. 4,255,053; Sengoku et al, U.S. Pat. No. 4,299,487; Sagusa et al, U.S. Pat. No. 4,318,615.

SUMMARY OF THE INVENTION

In the system of the present invention, the previously centrifuged tube containing the solute to be studied is vertically supported in the path of the monochromatic beam of a spectrophotometer. The tube is mounted in a transparent cuvette which is moved vertically by a platform member which is driven by a variable-speed motor assembly at a known uniform rate, or in time-controlled vertical steps. The light is transmitted through the vertical centrifuge tube via a stationary horizontal slit. The transmitted light impinges on a photo detector, which provides absorbance vs. time readings during a scanning cycle defined by the vertical movement of the centrifuge tube. The data comprising absorbance vs. time through the scanning cycle are processed digitally. (The time data are converted to vertical position data). A microcomputer is used to control the scanning motor drive, to collect the absorbance data, to convert the relative time of data collection to the corresponding radial position in the centrifuge, and to calculate the molecular weight or sedimentatin coefficient from these data.

The above-defined optical scanner structure is designed to move the centrifuge tube in a vertical direction past the stationary horizontal slit at fixed velocity. In a typical device the slit is 0.5 mm wide. The intensity of the monochromatic light (visible or UV) passing through the slit and centrifuge tube is measured by a photomultiplier or photodiode and is converted to an apparent absorbance which is collected and stored digitally at fixed time increments (typically one reading per second). In the case of continuous movement of the tube, the speed with which the tube moves past the slit may be adjusted to provide, for example, between 30 and 150 readings of absorbance vs. time, depending upon the volume of the sample and the resolution desired. The closure of the microswitch at the end of the vertical travel of the centrifuge tube serves to halt the scanner drive, to mark the vertical position of the tube relative to the slit at that point, and to initiate the next stage of data processing.

As previously mentioned, a microcomputer is employed for recording and processing the data digitally. A graphic display and hard copy device may be employed, but are not essential.

The microcomputer calculates the radial position of a volume element whose absorbance was measured. If a sedimentation equilibrium experiment was performed, a graph of the natural logarithm of the absorbance vs. the squared radial position of the corresponding volume element in the centrifuge is plotted on the CRT display of the microcomputer. From the slope of the plot on the additional information requested from the user, the molecular weight of the solute is calculated and displayed by the microcomputer. If a sedimentation velocity experiment was performed, a graph of the absorbance versus radial position of the corresponding volume element in the centrifuge is plotted on the CRT display. From the shape of this plot and additional information requested from the user, the sedimentation coefficient of the solute is calculated and displayed by the microcomputer.

Accordingly, a main object of the invention is to provide an improved system for determining the molecular weight or sedimentation coefficient of macromolecules via sedimentation equilibrium in a centrifuged tube, which overcomes the disadvantages and deficiencies of the previously used systems.

A further object of the invention is to provide a novel and improved method and means for measuring the dependence of solute concentration upon position in a non-uniform solution.

A still further object of the invention is to provide an improved system for moving a centrifuged sample in an optically transparent centrifuge tube past a stationary slit in the optical path of the spectrophotometer so as to define a scanning apparatus to measure the absorbance at various levels of the centrifuged sample, providing data for calculating the molecular weight of macromolecules in the sample, said improved system being usable without requiring variation of the light path with the position of the sample being scanned, thereby enabling the use of a relatively simple and inexpensive mechanical and optical apparatus for scanning.

A still further object of the invention is to provide an improved optical cell scanner which can be used outside of a centrifuge to quantitate the gradient of solute established in a centrifuge tube during centrifugation.

A still further object of the invention is to provide an improved system combining the use of a spectrophotometer, a scanning accessory and a microcomputer to perform the necessary measurements and data processing, in an integrated fashion, to determine the molecular weight and/or sedimentation coefficient of macromolecules via measurement of sedimentation equilibrium or velocity in a centrifuge tube.

BRIEF DESCRIPTION OF THE DRAWINGS

Further objects and advantages of the invention will become apparent from the following description and claims, and from the accompanying drawings, wherein:

FIG. 2 is a schematic diagram of a spectrophotometer provided with a typical centrifuge tube scanning device employed in the system of FIG. 1.

FIG. 5 is an enlarged perspective view of an assembled cuvette, tube holder and centrifuge tube, employed with the scanning accessory of FIGS. 3 and 4.

FIG. 6 is an enlarged front elevational view of a slit mask employed in the scanning accessory of FIGS. 3 and 4.

DETAILED DESCRIPTION OF PREFERRED EMBODIMENTS

Figure 1:
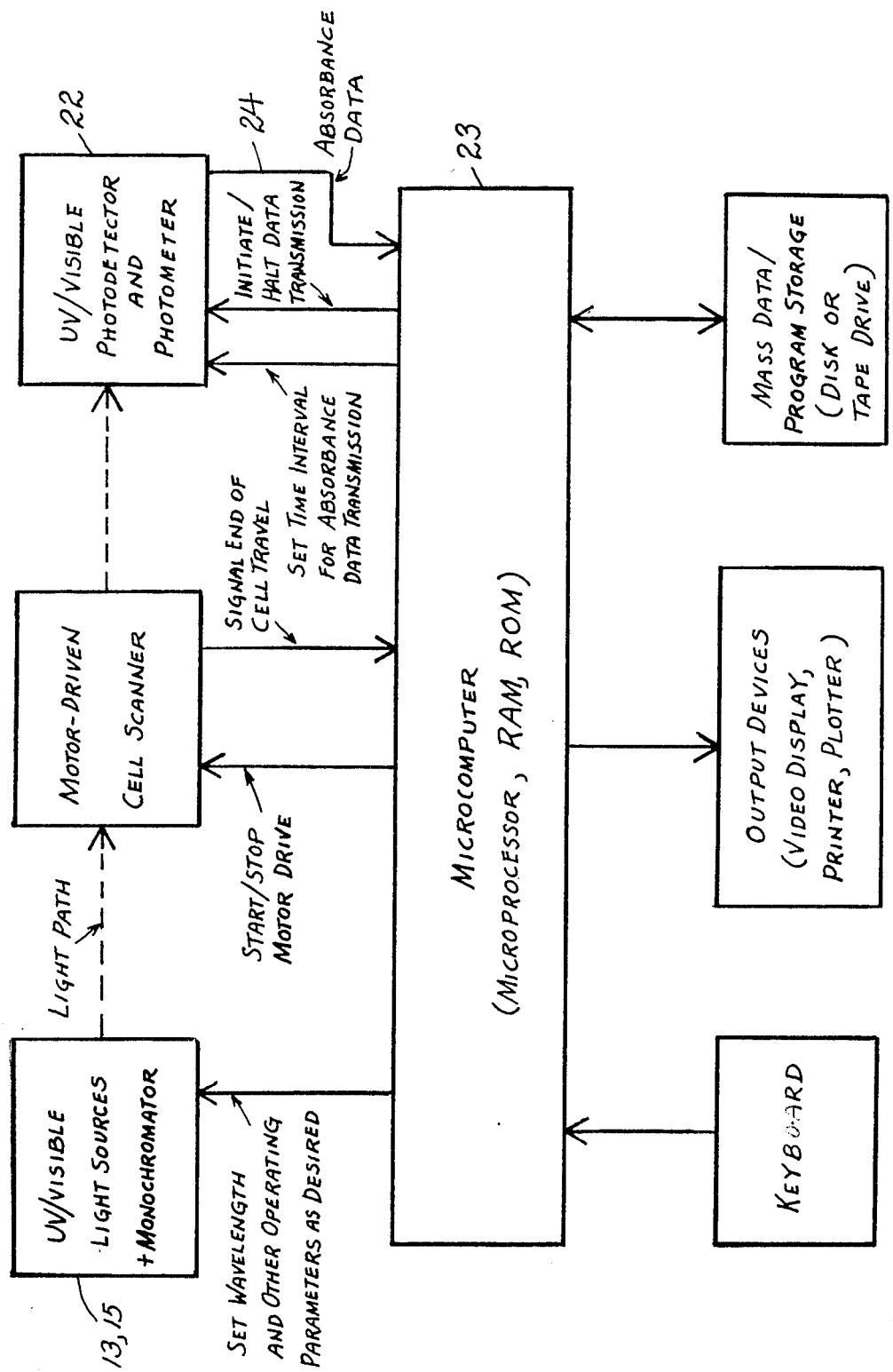
FIG. 1 is a block diagram of an improved combined system according to the present invention, for performing the necessary measurements and data processing for determining the molecular weight of macromolecules via sedimentation equilibrium in a centrifuge tube.

Referring to the drawings, and more particularly to FIG. 2, a typical optical scanning arrangement according to the present invention may comprise a conventional spectrophotometer combined with transport means for moving a quartz centrifuge tube 11 vertically through the stationary sample-absorbance beam 12 of the tube spectrophotometer. A light source 13 provides an output beam 14 which passes through a monochromator 15 to provide a resultant selected monochromatic beam 16, which in turn passes through a beam splitter 17, forming a reference beam 18 and the sample probe beam 12. Reference beam 18 impinges on a reference photodetector 19 to form a reference signal with which the spectrophotometer output absorbance signal is compared in a conventional manner. Beam 12 passes through a stationary horizontal slit 25 in a slit mask 26 and through a transparent cuvette 20 supportingly containing the quartz sample tube 11. The resulting absorbance beam 21 impinges on a conventional photodetector 22, forming an absorbance signal which is furnished to a microcomputer 23 (FIG. 1) via a data line 24.

The cuvette 20 is supported on a platform element 27 which is vertically movable but is held against rotation, for example, by a depending vertical arm 28 engaging slidably against the straight edge of a fixed horizontal flange 29 forming part of the frame of the apparatus. A vertical screw 30 is rigidly secured to and depends from platform element 27 and is threadedly engaged through a driven gear 31 rotatively and retentively mounted on flange 29. Gear 31 is in mesh with a suitably journalled driving gear 32 which is in turn drivingly coupled to a variable speed drive motor assembly 33 controlled by the microcomputer 23.

A microswitch 34 is mounted in a position to be closed responsive to the elevation of the cuvette 20 to its upper limit and to operate a relay circuit which signals the microcomputer 23 to stop the drive motor.

The structure of the cuvette transport mechanism shown diagrammatically in FIG. 2 merely represents one possible arrangement for raising and lowering the cuvette 20 via the action of the gearing 32,31 and the cooperating elevating screw 30 fixed to the supporting platform of the cuvette. A preferred modified arrangement will be presently described.

Typical operation is as follows: The user puts between 30 and 100 microliters ml of solution containing a single macromolecular solute into a quartz centrifuge tube 11. The macromolecular species should be sufficiently concentrated so that it contributes an absorbance of at least 0.1 absorbance unit per cm at the wavelength selected for monitoring the concentration. A small concentration (typically 2.5 to 5 mg/ml) of an inert low molecular weight solute, such as sucrose, may be added to stabilize the macromolecular concentration gradient. The sample is spun in an ultracentrifuge for the length of time and at the angular velocity appropriate to the type of experiment being performed (i.e., sedimentation equilibrium or velocity). When the run is concluded, the centrifuge rotor is slowly brought to a halt and the tubes are removed gently to avoid mixing of the tube contents.

A tube 11 (in a cuvette 20) is placed in the spectrophotometer, with the wavelength of light adjusted to correspond to a selected absorption maximum, and the scan is initiated. The apparent absorbance is measured as a function of time relative to the moment at which the microswitch 34 signalling the end of the scan is activated. A typical scan requires 1 to 2 minutes. Following the sample scan, the tube 11 is washed, filled with solvent, and replaced in the scanner in the same orientation as before. A second scan is made to record the background, which is automatically subtracted from the previously stored scan to eliminate artifacts arising from optical inhomogeneities in the centrifuge tube and refraction of the light beam by the cylindrical tube.

The following calculations are then performed by the microcomputer 23: The time at which an absorbance reading was made relative to the termination of the scan is converted to the vertical position of the volume element whose absorbance was measured, and, by means of an easily derived user-supplied algorithm for the particular centrifuge used (This algorithm is dependent on the rotor and centrifgue geometry.), the radial position of tha volume element in the centrifuge. If desired, a table of the radial position, the absorbance, the squared radial position, and the natural logarithm of the absorbance for each data point may be printed. A graph may then be plotted of the natural logarithm of the absorbance vs. the squared radial position. According to the theory of sedimentation equilibrium, this plot should be linear for a dilute solution of a single macromolecular species, and the slope of the plot will be proportional to the molecular weight of this species. If the plot appears satisfactory to the user he may request the microcomputer to calculate the molecular weight of the solute. The microcomputer then calculates the least-squares best fit straight line through the data points or any portion of the data selected by the user, requests from the user additional information needed to calculate the molecular weight (temperature, rotor speed, partial specific volume), and calculates and displays the molecular weight. A CRT plot of a graph of the natural logarithms of the absorbance readings vs. the squared radial positions of the volume elements over a test range, typical for the claimed invention, reproduced in FIG. 7. As above stated, the slope of the plot is proportional to the molecular weight of the single macromolecular species for which the measurements were taken.

If a sedimentation velocity experiment has been performed, then a graph of absorbance versus radial position is plotted on the CRT display. If the plot appears satisfactory to the user, he may request the microcomputer to calculate the sedimentation coefficient of the solute. The user is then asked to bracket the data points corresponding to the upper meniscus of the sample and to bracket the data joints corresponding to the trailing boundary of the solute by manipulating a graphics cursor on the displayed graph. Additional information (temperature, rotor speed, duration of run, partial specific volume) is then requested from the user, and the microcomputer calculates and displays the sedimentation coefficient.

Figure 3:
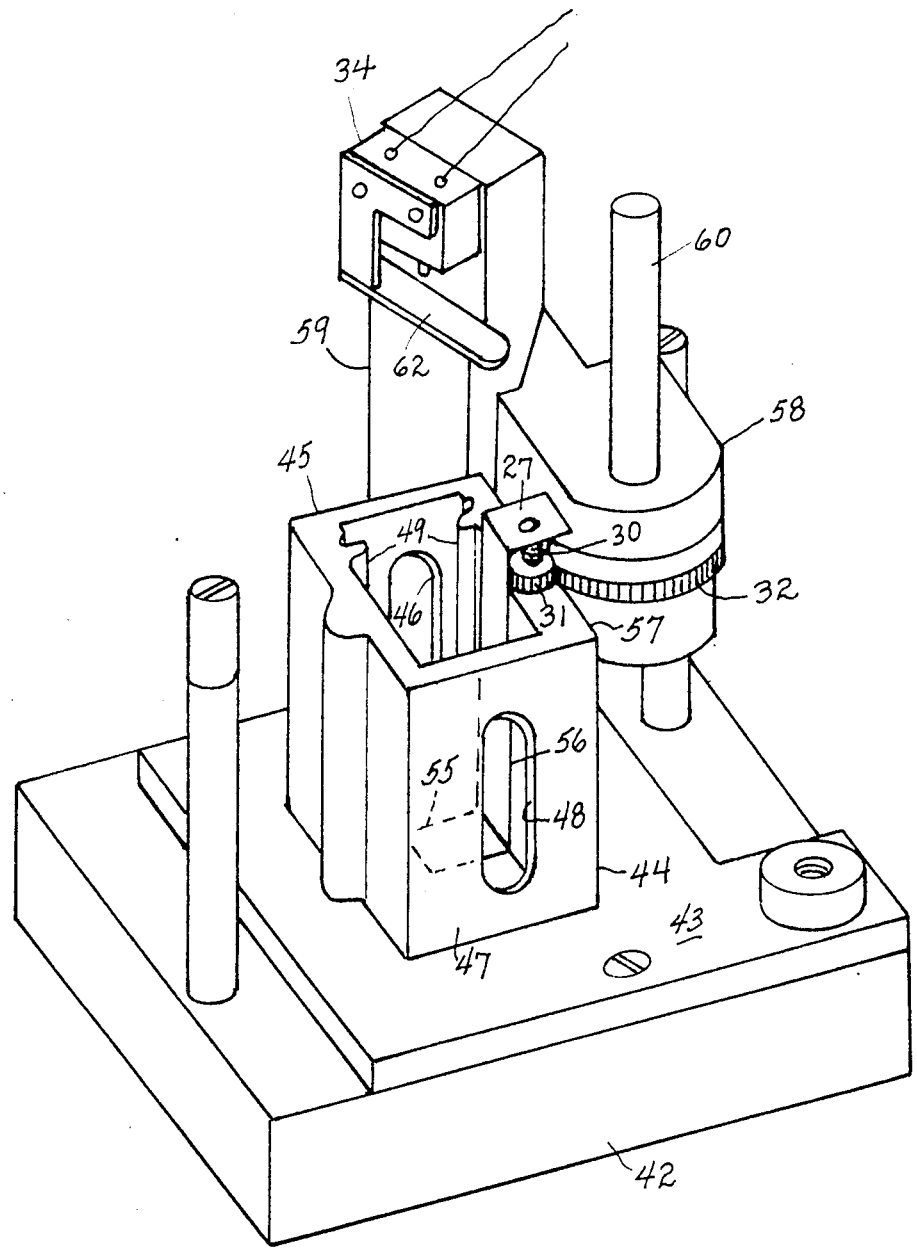
FIG. 3 is an enlarged perspective view of the main component of a specific embodiment of a centrifuge tube scanning accessory employed in a system as shown in FIG. 1.

Referring to FIGS. 3 and 6, a further embodiment is illustrated, in the form of a scanning accessory 36 which may be employed with a conventional spectrophotometer. The scanning accessory 36 comprises a generally rectangular housing 37, provided with a top cover, not shown, to make the housing substantially light-tight during operation of the apparatus. Suitable respective windows, shown diagrammatically at 38 and 39, are provided in the side walls 40 and 41 of housing 36 for the probe beam 12 and the exiting beam 21, attenuated by sample absorbance. The reversible, variable-speed motor assembly 33 is mounted on the side wall 41.

Figures 4, 7:
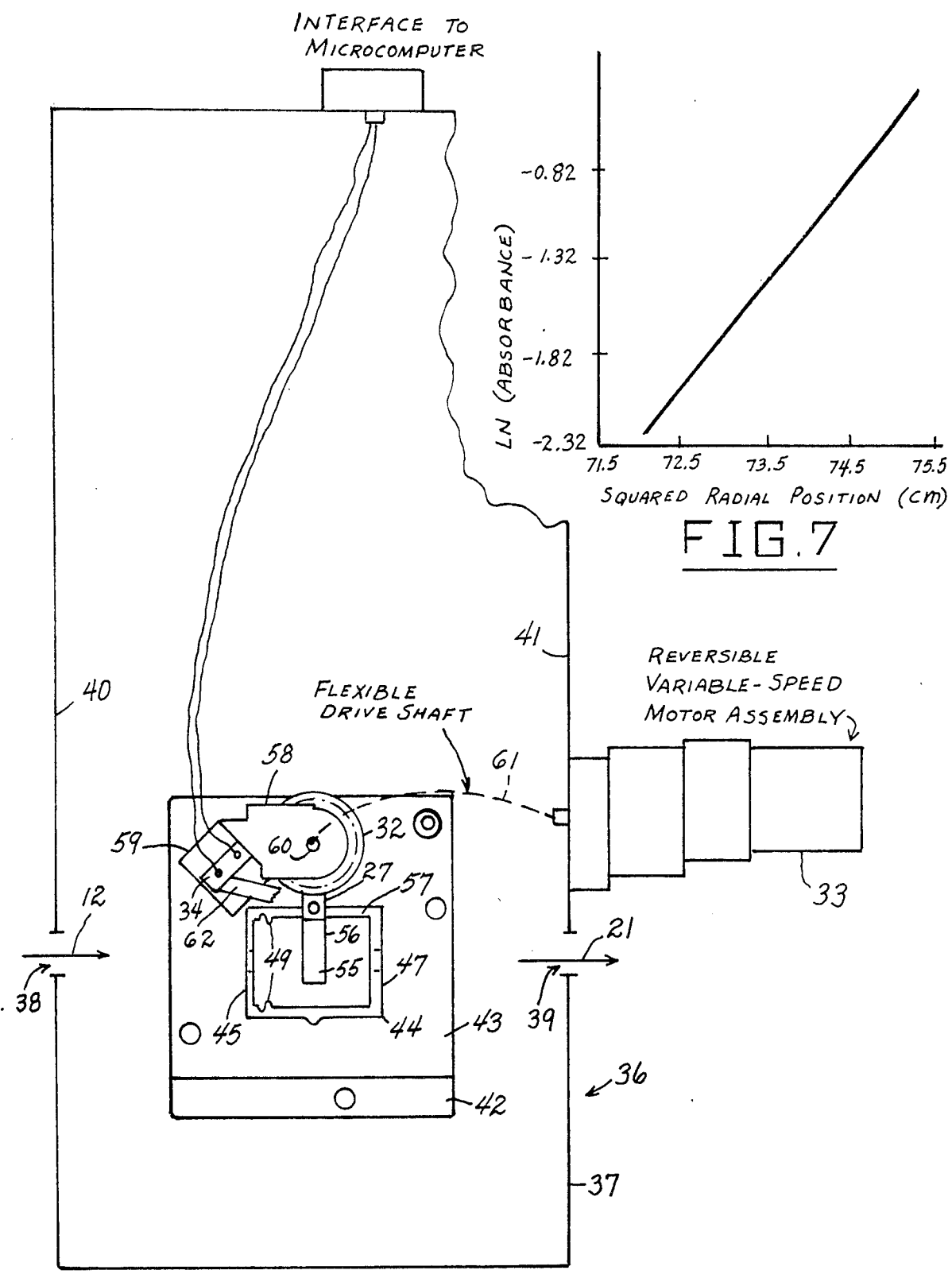
FIG. 4 is a top plan view, partly diagrammatic, of the scanning accesssory of FIG. 3, shown in its housing with its top cover removed and without its slit mask.
FIG. 7 is a graph showing a plot, typical for the claimed invention, of the natural logarithm of optical absorbance test readings vs. squared radial position of the corresponding volume element of a centrifuged sample over a test range.

Designated at 42 is a rectangular base block secured on the bottom wall of the housing 37 substantially midway between the optical windows 38 and 39. Secured on base block 42 is a plate member 43 formed with an integral upstanding, rectangular, opaque cuvette holder 44, aligned with the optical windows 38 and 39, and formed to slidably receive a sample cuvette 20, shown in enlarged detail in FIG. 5. The left vertical wall 45 of the holder 44, as viewed in FIG. 4, is formed with a centered vertical light-entry slot 46 facing window 38 (see FIG. 3), and the right vertical wall 47 thereof is formed with a centered exit slot 48, which is parallel to slot 46 and which faces the exit window 39. The enclosure 44 is formed with integral, inwardly directed opposite vertical ribs 49, 49 adjacent to but spaced from wall 45 to define a retaining socket for a rectangular slit mask 26, shown in FIG. 6. When supported in said retaining socket, the horizontal slit 25 of the mask is substantially centered relative to the entry slot 46 and defines a fixed path for the probe beam 12 with respect to a centrifuge tube 11 supported in the cuvette 20.

The slit mask 26 is made of suitable opaque material, such as relatively thin, rigid blackened sheet metal. The slit 25 is dimensioned so as to restrict the incoming light beam to a substantially rectangular area approximately 0.5 mm wide and 1.5 mm long.

The cuvette 20 is of vertically elongated rectangular shape and is made of optical quartz. The cuvette is provided with an adaptor block 50 made of black plastic and formed with a transverse, light-transmission notch 51, which may be about 2 mm wide, with central opposing arcuate vertical grooves 52 shaped to conformably closely receive and support a centrifuge tube 11 in upright position, as shown in FIG. 5. A stainless steel lifting rod 53 is rigidly attached to a corner portion of block 50 and projects upwardly therefrom, rising above the open top end of the cuvette and being provided with a lifting handle ball 54, enabling easy replacement and removal of the centrifuge tube 11.

The cuvette 20 is slidably receivable in the rectangular space defined between vertical ribs 49, 49 and the opposite side wall 47 of holder 44, and is supported on the bottom horizontal arm 55 of a generally Z-shaped bracket member 56. Bracket member 56 has a vertical main portion slidably interengaged with a shallow vertical groove in the rear vertical wall 57 of holder 44. The Z-shaped bracket member 56 has a top arm 27 having a depending elevating screw 30 rigidly secured thereto. Screw 30 is threadedly engaged with a small gear 31 journalled retentively to the top portion of rear wall 57. Gear 31 is drivingly meshed with a large gear 32 journalled in an arm 58 projecting horizontally from an upstanding post member 59 rigidly secured on plate member 43. Gear 32 has an upwardly projecting vertical shaft 60 which is drivingly coupled to the reversible, variable-speed motor assembly 33 by a detachable flexible drive shaft 61.

A conventional microswitch 34 is secured to the top portion of post member 59. The microswitch 34 is provided with a resilient operating arm 62 which extends over the bracket top arm 27 and which is operatively engageable thereby at the designated upper limit of travel of the centrifuge tube 11 carried in its cuvette 20, so as to stop the upward movement of the scanned tube 11 in the manner previously described.

The drive motor assembly 33 may be used to raise the cuvette 20 in holder 44 at a constant velocity. The assembly 33 may normally employ a conventional synchronous motor. Alternatively, a stepping motor may be employed in place of the synchronous motor. The centrifuge tube 11 being scanned could then be moved past the slit 25 in an incremental fashion rather than at uniform velocity. At each incremental position absorbance data could be accumulated and averaged until any desired degree of precision was attained, before again incrementing the tube position. It is believed that the sensitivity of the procedure could thus be greatly increased, whereby the amount of solute required to perform the measurement could be correspondingly greatly reduced.

The normal operation of the embodiment of FIGS. 3 to 6 may proceed as follows: The centrifuge tube 11 containing the sample is placed in the adaptor block 50 and the block, with the tube 11 therein, is inserted, via handle rod 53, into the cuvette 20. Said cuvette may contain a transparent liquid such as water, whose purpose is to reduce internal reflection and refraction of the light beam 12 by the cylindrical centrifuge tube. The upper portion of the centrifuge tube is suitably marked to facilitate replacement in the adaptor block 50 with the same orientation as in previous placements. The cuvette 20 containing the centrifuge tube 11 is then placed in the cuvette holder 44 and the gear drive 32, 31 is rewound to lower the cuvette 20 to its starting position. The compartment 47 is then closed by replacing its cover. At time "zero", the drive motor is started and the centrifuge tube 11 begins to rise at constant velocity (typically, 1 to 5 mm/min) relative to the slit aperture 25. As the tube rises, the light traversing the slit 25 passes through an element of sample volume which is closer to the bottom of the centrifuge tube. Thus, the dependence of apparent optical absorbance upon time as measured by the spectrophotometer, reflects the dependence of absorbance upon the height of the sample in the centrifuge tube. When the cuvette holder 44 reaches the top limit of its travel, the microswitch 34 is closed, activating a relay which halts the motor drive.

The above-described method of moving the sample in an optically transparent centrifuge tube past a stationary slit enables the scanning device to be simply and inexpensively constructed as an accessory for commercially available spectrophotometer. On the other hand, a scanning method involving the use of a slit which moves past a stationary sample would require that the light path vary with the position of the volume element of a sample being scanned, and consequently would necessitate a much more complex mechanical and optical design.

While certain specific embodiments of an improved system for the determination of molecular weights and/or sedimentation coefficient of optically absorbing solute material have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A method of measuring the concentration gradient of solute in solution with a solvent in an optically transparent cylindrical centrifuge tube having a concentration gradient of solute along the cylindrical axis of said centrifuge tube, comprising
   (a) fitting said centrifuge tube, with said concentration gradient of solute therein, into a holder having a cylindrical bore, defined by a non-reflective bore surface, adapted for tightly fitting said centrifuge tube therein, an exterior shape having two parallel faces and a pair of vertical slits through said parallel faces of said exterior shape defining a transverse radiation passage including, when said centrifuge tube is fit into said cylindrical bore, said centrifuge tube;
   (b) placing said holder, with said centrifuge tube therein, in an upright position into an optically transparent cuvette having flat parallel faces and an interior shape which is essentially the same as that of said exterior shape of said holder and being of an internal diameter slightly larger than that of said holder so as to securely position said holder in said cuvette interior;
   (c) supporting the cuvette, with said holder and said centrifuge tube therein, in an upright position;
   (d) passing a fixed beam of radiant energy transversely through the upright cuvette, with said holder and said centrifuge tube therein, along said transverse radiation passage;
   (e) moving said cuvette, with said holder and said centrifuge tube therein, axially through a range of movement; and
   (f) measuring the absorbancy of said fixed beam at a plurality of positions along said range of movement.

2. The method of claim 1, further comprising the step of filling space between said holder and said cuvette with a transparent liquid for reducing internal reflection and refraction of light passing through said cuvette and said transverse radiation passage, said transparent liquid contacting said centrifuge tube.

3. The method of claim 2, further comprising the steps of subjecting said centrifuge tube, when containing only said solvent therein, to said steps (a) through (f) and subtracting, for each of said plurality of positions, the absorbancy of said centrifuge tube with only said solvent therein from the corresponding absorbancy of said centrifuge tube with said solute concentration gradient therein, whereby an absorbancy valve corresponding only to said solute concentration gradient, unaffected by inhomogeneities in said centrifuge tube, is obtained.

4. The method of claim 2 wherein said centrifuge tube comprises quartz.

5. A method of determining the molecular weight of macro-molecular solute material comprising the steps of:
   (a) centrifuging said macro-molecular solute in a optically transparent cylindrical centrifuge tube substantially to a condition of sedimentation equilibrium;
   (b) fitting said centrifuge tube, with said concentration of solute gradient therein, into a holder having a cylindrical bore defined by a non-reflective bore surface adapted for tightly fitting said centrifuge tube therein, an exterior shape having two flat parallel faces and a pair of vertical slits through said parallel faces of said exterior shape defining a transverse radiation passage including, when said centrifuge tube is fit into said cylindrical bore, said centrifuge tube;
   (c) placing said holder with said centrifuge tube therein in an upright position into an optically transparent cuvette having flat parallel faces and an interior shape which is essentially the same as that of said exterior shape of said holder and being of an internal diameter slightly larger than that of said holder so as to securely position said holder in said cuvette;
   (d) supporting the cuvette, with said holder and said centrifuge tube therein, in an upright position;
   (e) passing a fixed beam of radiant energy transversely through the upright cuvette, with said holder and said centrifuge tube therein, along said transverse radiation passage;
   (f) moving said cuvette with said holder and said centrifuge tube therein, axially through a range of movement; and moving said cuvette, with said holder and said centrifuge tube therein, axially through a range of movement, and;

(g) measuring the absorbancy of said fixed beam at a plurality of positions of the centrifuge tube along said range of movement, thereby enabling the determination of the gradient of solute concentration of the centrifuged solute material and the calculation of the molecular weight therefrom.

6. The method of claim 5, and wherein said fixed beam of radiant energy comprises monochromatic light.

7. The method of claim 5, and wherein the axial movement of the transparent container is at a uniform rate.

8. The method of claim 5, and halting the axial movement when the container reaches a predetermined limiting position relative to said beam.

9. The method of claim 5, wherein the container is supported in a vertical position and wherein said range of movement of the container is in a vertical direction.

10. The method of claim 5, and wherein said container is moved vertically through said plurality of positions in controlled increments.

11. The method of claim 5, and wherein said container is moved continuously through said range of movement.

12. The method of claim 5, and wherein the measured absorbance is recorded digitally at fixed time increments corresponding to said plurality of positions of the container.

13. Apparatus for measuring the concentration gradient of solute in a cylindrical, optically transparent centrifuge tube, formed by the prior application of a sedimenting force, comprising a holder having a cylindrical bore therein, said cylindrical bore being defined by a non-reflective bore surface and adapted for tightly fitting said cylindrical centrifuge tube therein, an exterior having flat parallel faces and a pair of vertical slits through said parallel faces of said exterior defining a transverse radiation passage, including the central axis of said cylindrical bore;

an optically transparent cuvette having flat parallel faces and an interior shape which is essentially the same as that of the exterior shape of said holder and being of an internal diameter slightly larger than that of said holder; means to move said cuvette, with said holder having said centrifuge tube therein, axially through a predetermined range of movement;

a source of radiant energy to direct radiant energy from said source through said cuvette and along said transverse radiation passage; and means to measure the absorbancy of said beam at a plurality of positions along said range of movement.

14. The apparatus of claim 13, and wherein said means to support said tube comprises transparent cuvette means shaped to conformably receive the tube and vertically movable platform means underlying said cuvette means.

15. The apparatus of claim 13, and wherein said means to support said tube comprises motor-driven vertically movable platform means underlying said cuvette means, and means to limit the vertical range of movement of said platform means.

16. The apparatus of claim 15, and wherein said platform means includes a vertical drive screw fixed thereto, driving gear means threadedly engaged with said drive screw, and an electric motor drivingly coupled to said driving gear means.

17. The apparatus of claim 13, and wherein said means to move the tube axially through said predetermined range of movement comprises platform means underlying said support means, vertical elevating means drivingly coupled to said platform means, an electric motor drivingly coupled to said elevating means, energizing circuit means connected to said motor, and limit switch means operable to deenergize said motor at a predetermined elevated position of said centrifuge tube.

18. The apparatus of claim 13, and wherein said source of radiant energy is monochromatic.

19. The apparatus of claim 13, and wherein said means to measure the absorbance comprises a photodetector aligned with said fixed path through the centrifuge tube, a microcomputer, and circuit means connecting the output of the photodetector to said microcomputer.

20. The apparatus of claim 13, and wherein said means to move said tube axially includes reversible, variable-speed motor means drivingly coupled to said means to support the tube in upright position.

21. The apparatus of claim 13, wherein said centrifuge tube is disposed within said cylindrical bore and said holder is disposed within said cuvette, and wherein space between said holder and said cuvette contains a transparent liquid for reducing internal reflection and refraction of light passing through said cuvette and said transverse radiation passage.

22. The apparatus of claim 21 wherein said exterior shape of the holder is rectangular.

23. The apparatus of claim 21, wherein said holder has vertically extending means for lifting said holder from inside said cuvette.

* * * * *